(12) United States Patent
Grim et al.

(10) Patent No.: US 7,513,881 B1
(45) Date of Patent: Apr. 7, 2009

(54) KNEE IMMOBILIZER (75) Inventors: Tracy E. Grim, Thousand Oaks, CA
(US); Stacy Wyatt, Camarillo, CA (US);
Joseph M. Iglesias, Newbury Park, CA
(US); Wendee Lee, West Hills, CA (US);
Hugo A. Cobar, Tarzana, CA (US)

(73) Assignee: Ossur HF, Reykjavik (IS)

( * ) Notice: Subject to any disclaimer, the term of this patent is extended or adjusted under 35 U.S.C. 154(b) by 473 days.

(21) Appl. No.: 11/035,133

(22) Filed: Jan. 12, 2005

(51) Int. Cl.
*A61F 5/00* (2006.01)
*A61F 13/00* (2006.01)
*A61F 13/06* (2006.01)
*A61F 5/37* (2006.01)

(52) U.S. Cl. .................. 602/26; 602/5; 602/23; 602/62; 128/882

(58) Field of Classification Search ............... 602/5–6, 602/16, 23, 26, 62; 2/22, 24; 128/105.1, 128/882; 623/28, 30–31
See application file for complete search history.

(56) References Cited

U.S. PATENT DOCUMENTS

| 183,376 | A | * | 10/1876 | Darrach ............... 602/26 |
| 552,143 | A | | 12/1895 | Rankin |
| 3,304,937 | A | | 2/1967 | Callender, Jr. |
| 3,526,222 | A | | 9/1970 | Dreibelbis |
| 3,831,467 | A | | 8/1974 | Moore |
| 3,933,154 | A | | 1/1976 | Cabansag |
| 3,935,858 | A | | 2/1976 | Harroff |
| 3,958,567 | A | | 5/1976 | Callender, Jr. |
| 4,041,940 | A | * | 8/1977 | Frankel et al. ........... 602/26 |
| 4,050,455 | A | * | 9/1977 | Smith .................. 602/16 |
| 4,090,508 | A | | 5/1978 | Gaylord, Jr. |
| 4,111,194 | A | | 9/1978 | Cox et al. |
| 4,198,964 | A | * | 4/1980 | Honneffer ............. 602/19 |
| 4,388,920 | A | | 6/1983 | Hajost et al. |
| 4,407,276 | A | | 10/1983 | Bledsoe |

(Continued)

FOREIGN PATENT DOCUMENTS

DE    3520939 A1    12/1986

(Continued)

OTHER PUBLICATIONS

U.S. Appl. No. 10/675,324, filed Sep. 29, 2003, Cormier et al.

(Continued)

*Primary Examiner*—Patricia M Bianco
*Assistant Examiner*—Brandon Jackson
(74) *Attorney, Agent, or Firm*—Bacon & Thomas, PLLC (57) ABSTRACT

An orthopedic brace designed to immobilize the knee by preventing flexion/extension and limiting medial/lateral movement. The brace includes a main support structure embodied in a unitary, rigid stay member with slidable, semi-rigid cuffs at one or both ends to provide length adjustability. The stay member has no popliteal articulation in order to immobilize the knee joint, and further provides attachment for a Velcro strapping system for easy application to the posterior of the leg. A breathable foam softgood insulates the leg and knee from the main support structure and strapping system yet is completely detachable from the brace so it can be trimmed to any desired length or width, and washed as necessary.

22 Claims, 7 Drawing Sheets

U.S. PATENT DOCUMENTS

| | | | | |
|---|---|---|---|---|
| 4,776,326 A | | 10/1988 | Young et al. | |
| 4,796,610 A | * | 1/1989 | Cromartie | 602/26 |
| 4,844,326 A | | 7/1989 | Kashihara et al. | |
| 4,848,326 A | | 7/1989 | Lonardo | |
| 4,981,132 A | | 1/1991 | Chong | |
| 4,982,732 A | * | 1/1991 | Morris | 602/16 |
| 5,007,415 A | | 4/1991 | Marion | |
| 5,088,479 A | | 2/1992 | Detoro | |
| 5,116,296 A | * | 5/1992 | Watkins et al. | 482/91 |
| 5,230,335 A | | 7/1993 | Johnson, Jr. et al. | |
| 5,230,700 A | | 7/1993 | Humbert et al. | |
| 5,267,949 A | | 12/1993 | De La Torre et al. | |
| 5,385,534 A | * | 1/1995 | Cassford | 602/15 |
| 5,387,185 A | * | 2/1995 | Johnson et al. | 602/26 |
| 5,401,235 A | | 3/1995 | Devens | |
| 5,486,157 A | | 1/1996 | DiBenedetto | |
| 5,545,127 A | | 8/1996 | DeToro | |
| 5,554,104 A | | 9/1996 | Grim | |
| 5,571,206 A | | 11/1996 | Varn | |
| 5,593,383 A | * | 1/1997 | DeToro | 602/27 |
| 5,732,411 A | | 3/1998 | Coleman et al. | |
| 5,788,658 A | * | 8/1998 | Islava | 602/18 |
| 5,823,931 A | * | 10/1998 | Gilmour | 602/24 |
| 5,908,398 A | | 6/1999 | DeToro | |
| 5,944,679 A | | 8/1999 | DeToro | |
| 6,200,286 B1 | * | 3/2001 | Zamani | 602/64 |
| 6,302,858 B1 | | 10/2001 | DeToro et al. | |
| 6,350,246 B1 | | 2/2002 | DeToro et al. | |
| 6,377,178 B1 | | 4/2002 | DeToro et al. | |
| 6,383,156 B1 | | 5/2002 | Enzerink et al. | |
| 6,464,659 B1 | | 10/2002 | DeToro et al. | |
| 6,592,539 B1 | * | 7/2003 | Einarsson et al. | 602/62 |
| 6,719,713 B2 | | 4/2004 | Mason | |
| D496,464 S | | 9/2004 | Iglesias et al. | |
| 6,821,261 B2 | | 11/2004 | Doty et al. | |
| 7,011,641 B1 | * | 3/2006 | DeToro et al. | 602/26 |
| 7,122,016 B1 | * | 10/2006 | DeToro et al. | 602/26 |
| 7,128,723 B2 | * | 10/2006 | Doty et al. | 602/16 |
| 2002/0072695 A1 | | 6/2002 | Doty et al. | |
| 2002/0183672 A1 | | 12/2002 | Enzerink et al. | |

FOREIGN PATENT DOCUMENTS

| | | |
|---|---|---|
| WO | WO 93/15251 A1 | 8/1993 |

OTHER PUBLICATIONS

*Celebrating The Introduction of The KMO® Knee Management Orthosis*, Anatomical Concepts, Inc., Product brochure.

\* cited by examiner

FIG. 12

KNEE IMMOBILIZER

BACKGROUND OF THE INVENTION

The present invention is directed to an orthopedic brace. More precisely, the present invention is directed to a knee immobilizer.

The knee is probably the least protected joint in the human body. There is no ball and socket or mortice to hold the ends of the femur and tibia in their place. There are simply a few ligaments to hold everything together. Yet the knee carries the weight of our bodies and thus is subjected to more forces than any other joint in our anatomy.

The knee allows free flexion and extension of the lower leg and limited medial and lateral movement (rotation). If enough force is applied to the knee this rotation will increase and damage or tear the supporting ligaments. Damage can also result from the knee being bent backwards (hyperextension).

Once damage is done to the ligaments, the injured tissue needs time to heal. In many cases, simple rest is inadequate and surgery may be required to repair the damage. The present invention relates to a knee support that is worn to immobilize the knee after an injury as a form of treatment or as a temporary measure to prevent further injury before other treatments can be applied.

Most conventional knee immobilizers or braces on the market today are no different than the ones sold 20 years ago. They are simply pieces of foam with straps and pockets attached by sewing. Usually there are three pockets—one behind the knee (posterior), and one on each side of the knee (medial and lateral). Metal stays are inserted into these pockets to provide support and immobilization to the knee.

These conventional designs have several disadvantages. For example, they have a multitude of straps that make the knee brace confusing to use and time consuming to apply. Once the brace is applied to the leg, it tends to "piston" or migrate down the patient's leg because the medial/lateral stays are straight and do not follow the contours of the leg. Once the brace migrates out of position relative to the knee, the intended function is greatly reduced. Finally, conventional knee braces are not size/color adjustable so that medical practices must stock a multitude of sizes and colors as needed to fit the varying anatomy of their patients. These and other problems associated with conventional knee braces are overcome in accordance with various embodiments of the present invention.

SUMMARY OF THE INVENTION

The present invention is directed to a knee immobilizer. In one preferred embodiment, the knee immobilizer has an adjustable length for supporting the leg of a patient and comprises an elongated stay member disposed posterior to the leg having a femoral portion, a tibial portion, and a non-articulating popliteal region therebetween; a femoral cuff slidably disposed on the femoral portion; a tibial cuff slidably disposed on the tibial portion; means for selectively setting the linear position of the femoral and tibial cuffs relative to the femoral and tibia portions; and at least one liner that at least partially envelopes the leg, disposed on at least one of the stay member, the femoral cuff, and the tibial cuff.

In one embodiment, fewer straps are required because the femoral and tibial cuffs are designed to wrap around and cradle the muscle bellies of the leg. The result is an increase in the level of support with fewer straps and no medial or lateral stays. This increased support and the absence of the medial and lateral stays, allow for a much closer fit to the patient's anatomy, thereby greatly reducing the pistoning of the brace relative to the leg during use.

The stay member has an engineered geometric shape following the contours of the leg that provides all the immobilization necessary and is set at a functional angle of immobilization. Therefore, no articulation or hinge is needed at the popliteal region of the knee joint for ensuring proper fit as can be seen in the prior art braces. No tools are necessary for adjusting and setting that articulation which is now omitted. Omitting the articulation also enhances the strength of the popliteal region under bending and torsion, thereby further protecting the injured knee from unintended motion. There is further no risk of the articulation loosening in use since the articulation is omitted.

In addition, the sliding cuff-posterior stay assembly provides length adjustment via a simple push button actuator. Being made preferably from a semi-rigid polymer, the cuffs have opposed flexible arms that at least partially circumscribe the patient's limb. In a preferred embodiment, these cuffs are attached to more rigid plastic and contains push button adjustment means for adjustment relative to the stay. Both adjustments are easily performed without tools and can be undertaken by the patient if necessary. Accordingly, the knee immobilizer can be custom tailored to fit the patient's leg regardless of his or her gender, height, girth, musculature, etc. Finally, the foam liner is fully detachable from the cuff-posterior stay assembly. Removal allows trimming of the liner to the appropriate length and width for each patient and, when laminated with two different colored materials, color options for the end user by simply reversing which side is facing out. The removable liner also allows for a different configuration of the brace without any liner at all. This embodiment would have just minimal or no padding over the cuffs and strategic portions of the straps and D-rings. Some advantages to this brace are that it feels cooler to a user when worn in warm climates and environments; it possesses a lower profile which would allow for fitting under the user's clothing; and it further reduces pistoning.

DETAILED DESCRIPTION OF THE PREFERRED EMBODIMENTS

Figure 9:
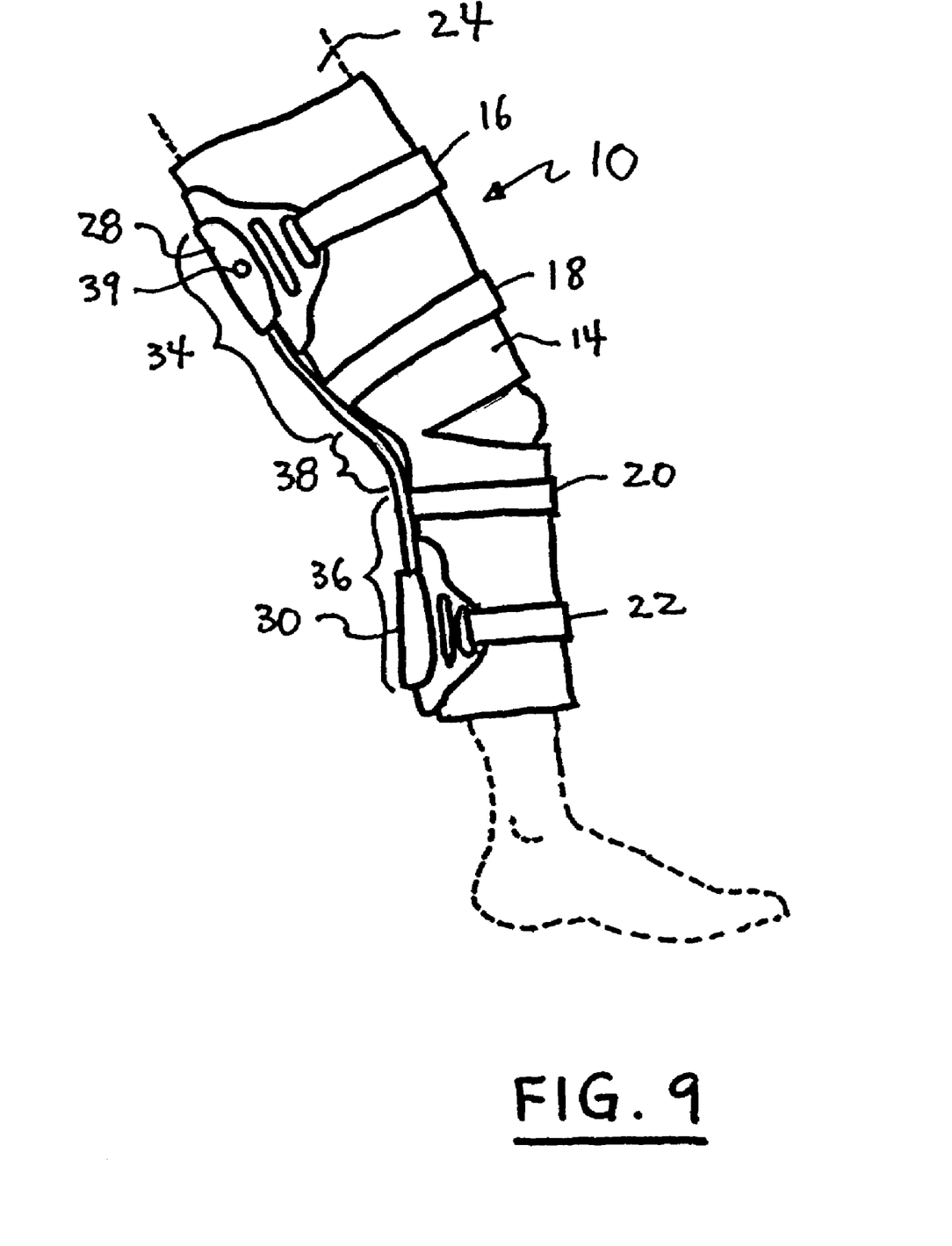
FIG. 9 is a side elevational view of the knee immobilizer is use on a leg of a patient shown in phantom lines.

The present invention is directed to an orthopedic brace for support of an injured limb. In the preferred embodiment, the present invention is directed to a knee immobilizer. As seen in the perspective view of FIG. 1, the knee immobilizer or brace 10 is preferably constructed of a rigid support structure 12 acting as a spine and incorporates an optional foam compressive liner 14 and a strapping system consisting of four straps 16, 18, 20, 22. As seen in FIG. 9, the knee immobilizer or brace 10 is shown in normal use. It is attached to the posterior portion of a patient's leg 24.

Figure 1:
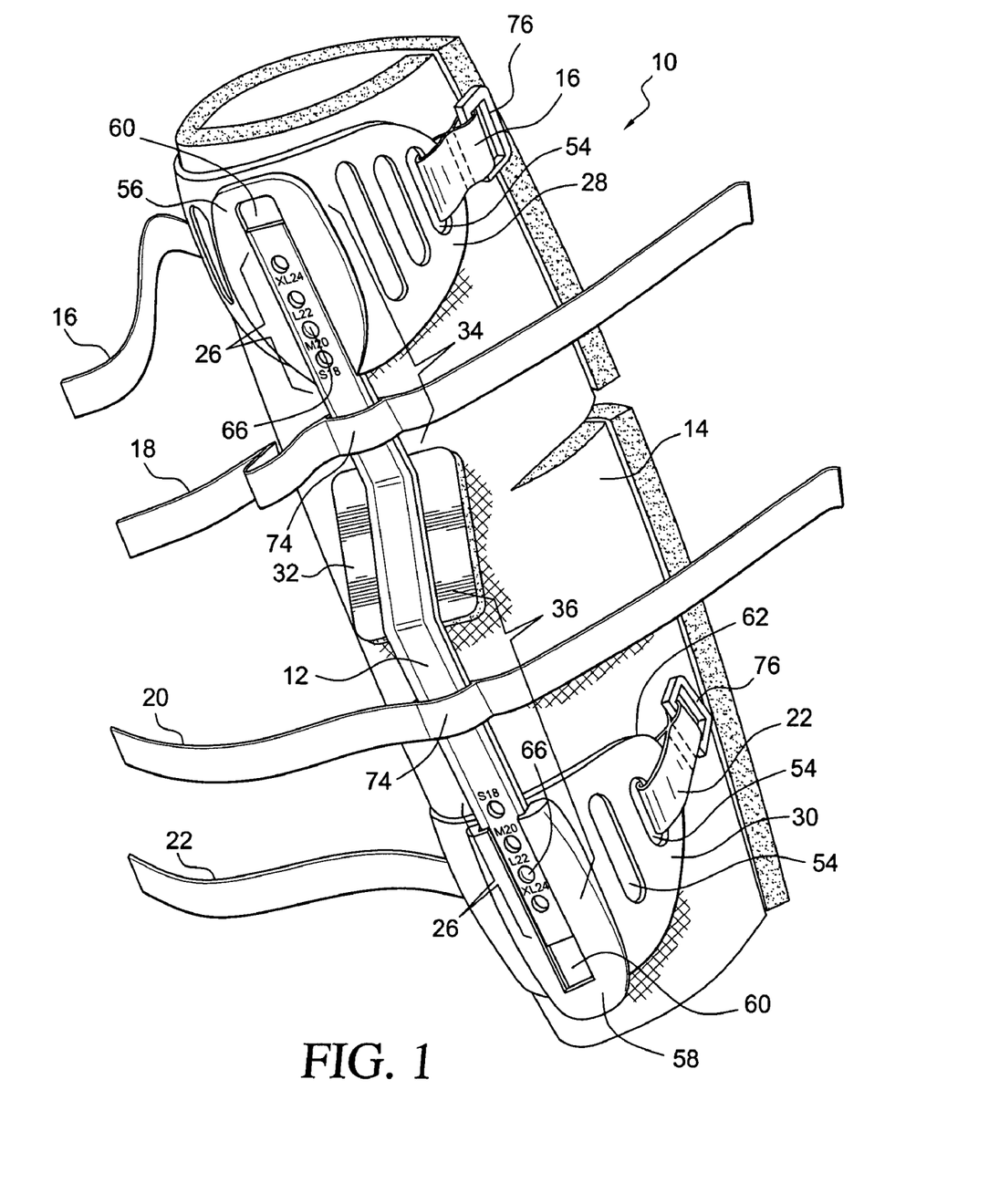
FIG. 1 is a perspective view of a preferred embodiment knee immobilizer.

In FIG. 1, at the top and bottom ends of the stay member 12 are the femoral and tibial cuffs 28, 30, respectively. The cuffs 28, 30 slide along the femoral and tibial portions 34, 36 of the stay member 12 for quick adjustment of its overall length. An optional popliteal pad 32 is attached to the stay member 12 to further provide support and protect the very sensitive popliteus area of the knee. The popliteal pad 32 is secured to the stay member 12 at the slightly bent popliteal region 38 in between the femoral portion 34 and the tibial portion 36, as best seen in FIG. 4(a).

The rigid stay member 12 resists bending and gives overall stability to the assembly, while the cuffs 28, 30 support and cradle the muscle bellies of the leg 24. The liner 14 with the straps 16, 28, 20, 22 comfortably and securely hold the entire assembly to the leg 24. When strapped together on the leg 24 as seen in FIG. 9, the components work together to immobilize the knee joint and to further prevent unintended rotation of the upper and/or lower portion of the limb that might further injure the knee. Since the popliteal region 38 has no articulation or hinge, the strength and stability in that region are superior to that of a conventional design, and there is virtually no possibility of the knee joint moving if the patient or user is ambulatory.

Figure 2:
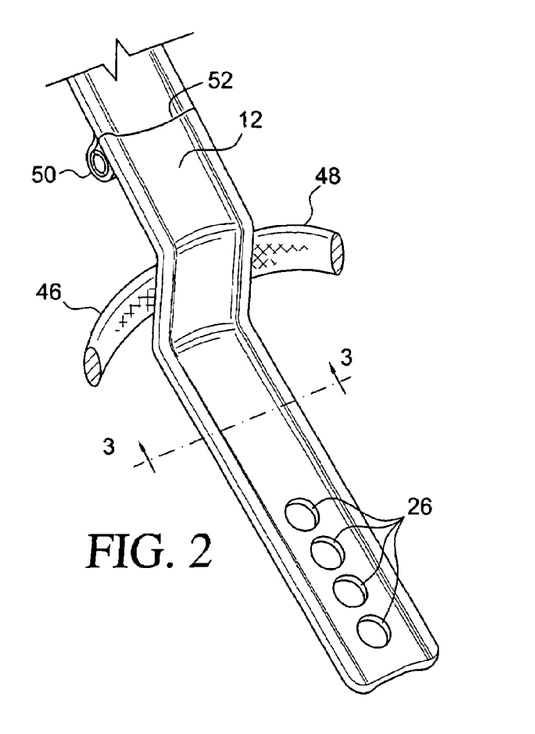
FIG. 2 is a perspective view of one end of a stay member having medial and lateral struts and a hinge away from the popliteal region of the knee joint.

As seen in the FIG. 1 embodiment, the rigid support structure is specifically a single-piece, rigid stay member 12 made from a unitary, uninterrupted-length bar of metal or high strength material. As shown in FIGS. 1 and 2, the stay member 12 has a series of oval holes 26 spaced apart in a specified increments preferably located at both ends of the stay member 12. The holes 26 allow the positions of the cuffs 28, 30 to be adjusted and set relative to the stay member 12. This adjustment extends or shortens the overall length of the brace 10 to quickly and easily tailor fitment of the knee immobilizer to the unique anatomies of patients of different sex, height, age, physique, weight, etc.

Figure 4A:
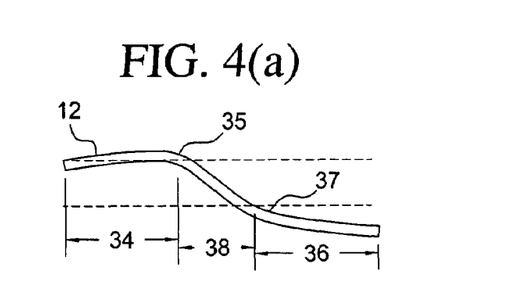
FIGS. 4(a) and 4(b) are side elevational views of two stay members.
Figure 4B:
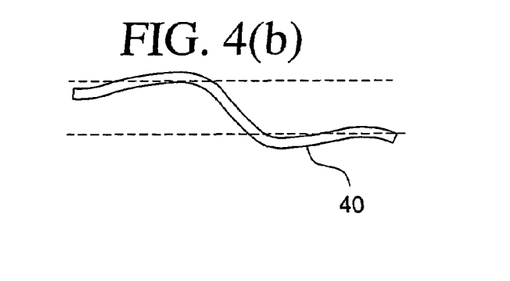

The stay member 12 is shown in a side elevational view of FIG. 4(a). The theoretical femoral portion 34, tibial portion 36 and popliteal region 38 are identified. A first curvature 35 is defined whereat the femoral portion 34 merges with the popliteal region 38, and a second curvature 37 is defined whereat the tibial portion 36 merges with the popliteal region 38. The two horizontal dashed lines are parallel and meant to contrast the preferred profile contour of the stay member 12, intended to closely follow the posterior contours of a human leg. Essentially, the stay member 12 begins as an extruded bar of aluminum having a straight profile, and is carefully fashioned with compound curves as shown in FIG. 4(a). FIG. 4(b) shows an alternative embodiment stay member 40 with a steeper bend in the popliteal region and less angular peaks and valleys.

Figure 3A:
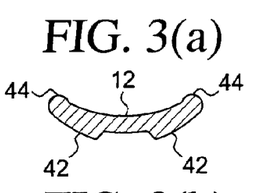
FIG. 3(a) is a cross-sectional view of the stay member taken at line 3-3.
Figure 3B:
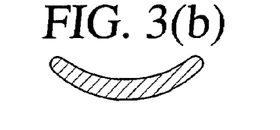
FIGS. 3(b)-3(i) are cross-sectional views of various alternative embodiment stay members.
Figure 3C:
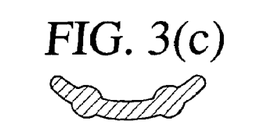
Figure 3D:
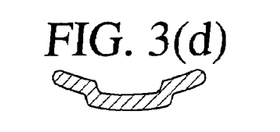
Figure 3E:
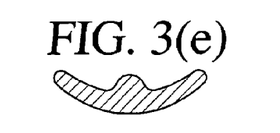
Figure 3F:
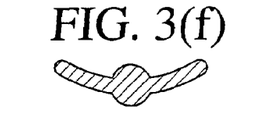
Figure 3G:
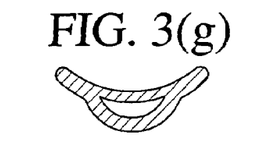
Figure 3H:
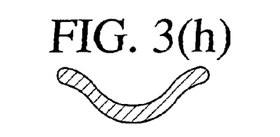
Figure 3I:
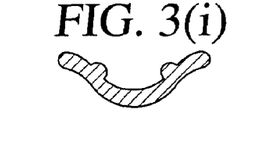

FIG. 3(a) is a cross-sectional view of the stay member 12 taken along line 3-3 in FIG. 2. In this cross-sectional view, it is clear that the stay member 12 has a bowed shape from edge to edge, and includes optional reinforced areas 42 underneath and reinforcement beads 44. This cross-sectional shape preferably runs uniformly from one end of the stay member 12 to the other. From empirical studies, the preferred embodiment stay member 12 shown in FIG. 3(a) has a cross-sectional shape that has been engineered to provide the ideal strength-to-weight-to-size ratio. It is preferable to minimize the depth of such a stay member in order to limit its effect and discomfort to the patient.

FIGS. 3(b)-3(i) illustrate the cross-sectional shapes of alternative embodiment stay members, some having a channel, reinforcement beads, etc. placed at different locations for best strength to weight ratio and optimum bending area moment of inertia. The stay member 12 may be a solid material or may have a hollow core at least for a lengthwise section thereof, as shown in the FIG. 3(g) embodiment. In the preferred embodiment, the stay member 12 is extruded from aluminum, but other high strength metals, laminated polymer composites, woven graphite, or fiber reinforced plastics or the like are contemplated. Furthermore, the polymers and metals can be integrated or laminated for different strength, weight, cost, durability, and other engineering considerations. The stay member may further take the form of bundled rods or multi-layer bars or any combination thereof. The rods or bars may be co-extruded with a polymer cladding in various alternative embodiments.

Preferably, the stay member should at least meet a bending load of about 25 ft-lbs. or more for knee immobilizers to be used by adults. Hence, the length, width, thickness, and cross-sectional area moment of inertia of the stay member should be considered to at least support such load bearing requirements. Furthermore, its length should be sufficiently long so that the femoral portion 34 and the tibial portion 36 extend well past the popliteus for comfortable load bearing of the body weight of the patient or user, and to provide sufficient slide adjustment motion for the cuffs 28, 30. In the preferred embodiments, the brace 10 spans from about 18 to 24 inches in overall length.

In the embodiment shown in FIG. 2, optional lateral and medial struts 46, 48, have been added to the support. These two struts 46, 48 are located on one or both sides of the knee, providing additional medial/lateral support and protection to the knee. The lateral and medial struts 46, 48 may be welded, bonded, Velcroed, fastened, or likewise mechanically attached to the stay member 12 or the liner 14. Each strut 46, 48 optionally has a slight forward curvature to at least partially circumscribe the knee. The forward curvature gives some protection from accidental external impact and further stabilizes the injured knee. The lateral and medial struts 46, 48 may be simple cantilevered bars as shown in FIG. 2, or may have a more integrated, complex form similar to the arches 78 shown in FIG. 10 except that the side hinges 82 are omitted.

Also shown in the FIG. 2 embodiment is an optional articulation or hinge 50 located away from the knee along the posterior of the leg. The hinge 50 allows the stay member 12 to break into two discrete sections along separation line 52 and linked only at the hinge 50. Once opened to a desired angle for the two sections, the hinge 50 can be locked down using a threaded nut or other means known in the art thus freezing the angle of the bend. The hinge 50 therefore gives greater adjustability to the stay member 12 for improved fitment to the hamstring area (or calf area if the hinge is located there) of the patient's leg.

In FIG. 2, the tibial portion 36 and its end are shown. Four holes 26a are cut, drilled, or otherwise formed into the stay member 12 for setting the location of the tibial cuff 30, mentioned earlier. In the preferred embodiment, there are four oval shaped holes equally spaced apart at each end of the stay member 12. Of course, the number, size, shape, and location of the holes can be modified from that shown to suit various design and engineering objectives. In one alternative embodiment (not shown), the stay member may have score marks, notches, grooves, or the like so that its length can be more easily shortened by breaking off a section at the score mark rather than sliding the cuff along the length of the stay.

Figure 5:
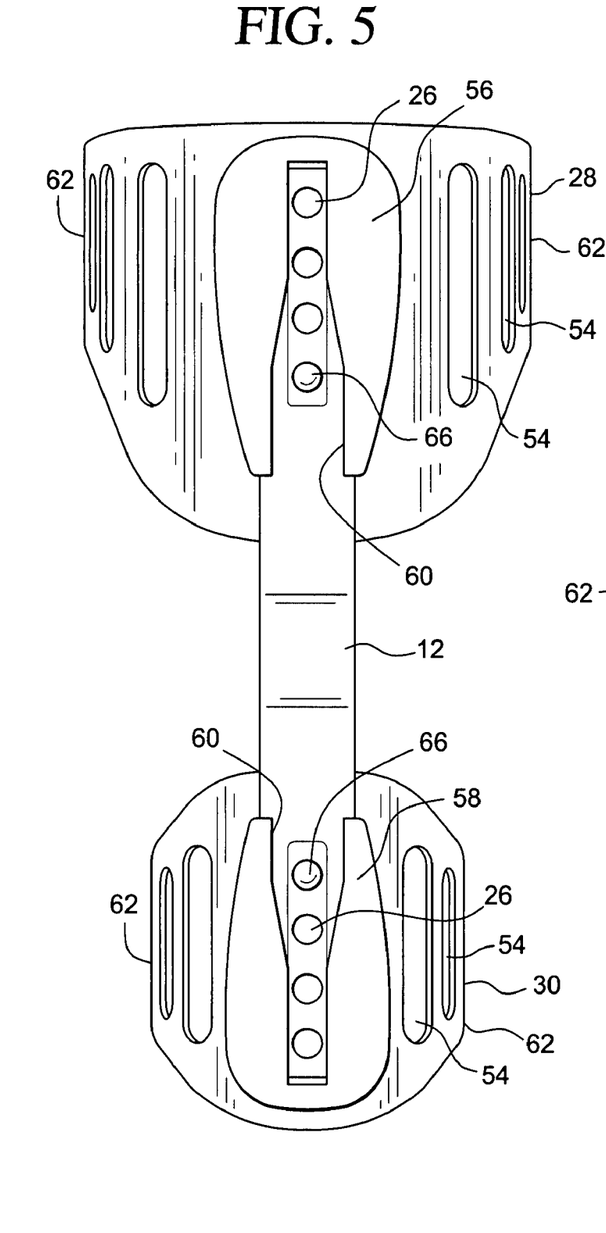
FIG. 5 is a rear elevational view of the stay member and cuff assembly without the liner.
Figure 6:
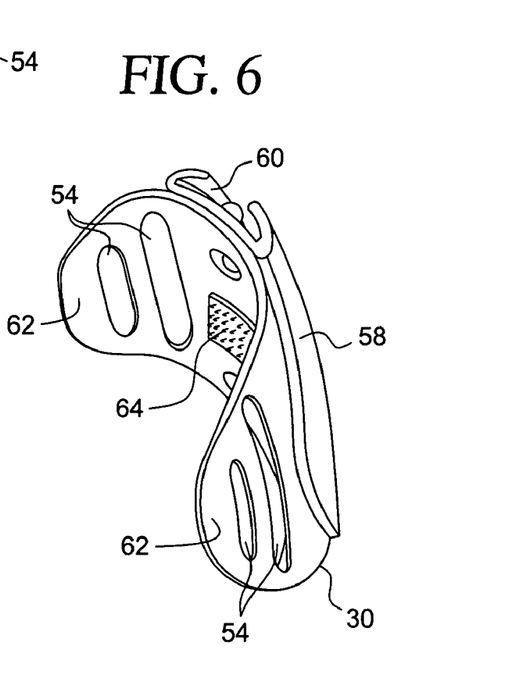
FIG. 6 is a perspective view of one cuff detached from the stay member.

FIG. 5 shows a rear view of the knee immobilizer with the liner 14 removed. Attached to the ends of the stay member 12 are the slightly larger femoral cuff 28 and the slightly smaller tibial cuff 30. FIG. 6 shows a single cuff 30 in a perspective view. These cuffs 28, 30 in a preferred embodiment are made of a semi-rigid plastic and are designed with strategically placed windows 54 to allow them to flex and shape around the anatomy of the leg. Preferably, the cuffs 28, 30 have a generally curved or arcuate shape to at least partially circumscribe the leg. The curvature may be molded into the material, or the cuff may be formed flat and the curvature created by pulling on securing straps.

In forming that arcuate shape, each cuff 28, 30 has opposed arms 62 with an optional curl. Within the opposed arms 62 are one or more windows 54. Also, the arms 62 may have a thinner wall thickness than at the common base of the curve. All together, the thinner wall at the arms 62 and the windows 54 where material has been removed provide flexibility and diametrical adjustability of the cuff 28, 30 for ideal user comfort and customized fitment to his or her leg. On the other hand, the bulkier base area of the cuff 28, 30 ensures stability and positive engagement when the cuff 28, 30 is assembled to the adjusters 56, 58 and stay member 12.

As seen in FIG. 6, the cuff 30 may have a patch of hook fastener material 64 for attachment of to the liner 14. The wall thickness change in the arms 62 may be gradual as shown, where the outer ends are the thinnest, or the change may be stepped. The size, location, and number of windows 54 may be altered from that shown. The preferred shape for the windows 54 is an elongated oval as shown, with the outermost windows 54 in the arms 62 being used for lacing one or more straps 16, 22 therethrough, as shown in FIG. 1.

In FIGS. 5 and 6, the cuffs 28, 30 are attached to the stay member 12 via a femoral adjuster 56 and a tibial adjuster 58. In the preferred embodiment, the adjusters 56, 58 are attached to each respective cuff 28, 30 by three rivets. Other means of attachment are contemplated, such as by bonding the parts together, snap fitting, welding, or forming the cuff and adjuster in a single integral piece.

In an alternative embodiment, the discrete adjuster and cuff are joined together by a hinge or pivot 39 as seen in FIG. 9. This way, when the knee immobilizer is worn by the user, the cuff has a slight rocking action to more readily adapt to the user's unique leg shape. Finally, although the preferred embodiment shown in FIG. 1 depicts only two cuffs, it is of course contemplated that the knee immobilizer may have only one cuff, or more than two cuffs depending on the treatment necessary to the injured knee, the unique anatomy and physical needs of the patient, etc.

Once assembled together, the stay member 12 easily slides inside the slots 60 created in each adjuster 56, 58, wherein the slots 60 are of the same shape as the outer surface of the stay member 12. With this arrangement, the adjusters 56, 58 enable each respective cuff 28, 30 to freely slide linearly along the ends of the stay member 12.

To achieve length adjustment of the knee immobilizer, the cuffs 28, 30 initially slide freely along the ends of the stay member 12. Once the ideal length adjustment is determined, the sliding action of the cuffs 28, 30 should be disabled. To do this, a means for setting the location of the cuffs 28, 30 relative to the stay member 12 is needed. In the preferred embodiment shown in FIGS. 1 and 5, a button assembly 66 is used, which includes a button and spring. The button assembly 66 is encapsulated between the cuff 28, 30 and adjuster 56, 58 during the riveting operation, wherein the button is biased by the spring into one of the holes 26 in the stay member 12 when the stay member 12 is located in the adjuster 56, 58. Accordingly, the length of the brace is adjusted by pressing the button down so the cuff assembly can be slid farther up or down the stay member 12. When the cuff assembly is adjusted so the next oval hole 26 is overlying the biased button, the spring forces the button up into that oval hole, thereby positively locking the location of the cuff 28, 30 on the stay member 12. This process is repeated until the desired size is achieved.

Beneficially, no tools or accessories are required for such an adjustment, and each cuff can be adjusted with one hand. The adjustment is simple enough so that it can be performed by a patient or user with no training.

Other means for setting the location of the cuffs 28, 30 relative to the stay member 12 and modifications thereto are contemplated. For example, the preferred embodiment can be modified to rearrange the relative locations of the button, spring, and holes. In this modification, the holes may be located along the edge of the stay member with a biased pin extending sideways through the adjuster into the selected hole thus locking the two together. Again, a positive mechanical engagement is achieved between the stay member and the cuff via the adjuster. Of course, as suggested above, the adjuster structure can be omitted and a simple slot can be formed integrally into the cuff.

In an alternative embodiment, a mechanical rack and pinion system can be used replacing the button assembly and holes, wherein the edges of the stay member have teeth that engage the complementary gear teeth of a rotating pinion, whose rotation can be locked down by a thumb screw to immobilize the overall relative sliding action. The pinion can be replaced by a movable finger attached to the cuff that is spring biased into the teeth at the edge of the stay member. Rocking the finger over a pivot point or similarly withdrawing the finger away from the teeth enables the sliding action between the stay member and cuff.

In yet another embodiment, a frictional lock can be used in the form of a pivoted lever that is rotated and wedged into contact with the stay member and the gripping contact surfaces are optionally covered with a high friction rubber or like grippy material. In still yet another alternative embodiment, a deadbolt system can be implemented similar to its operation in a door, wherein the deadbolt slides under spring bias into a receiving hole in the stay member thus positively locking the two together. Likewise, a stop or surface bump can be used in place of a hole.

Yet another alternative embodiment contemplates the stay member sliding inside the slot as shown in FIG. 1, but the button assembly is replaced with a threaded thumb screw whose shaft extends through one of the holes or a longitudinal slot in the stay member. The tip of the advancing thumb screw can be threaded into a corresponding hole, groove, or stop in the cuff or adjuster. If the holes are replaced with a slot in this embodiment, the stop settings are not limited to four or however many holes are present but would be technically infinitely adjustable. The tip of the threaded shaft may have a rubber cap to improve grip or wedging action, and to minimize damage to the stay member if the user overly torques the thumb screw. All such similar mechanical locking mechanisms are contemplated.

In various alternative embodiments, the adjuster can be welded, bonded, or permanently secured or affixed to the stay member at one end thereof eliminating the slide adjustment while the opposite end of the stay member has a cuff that remains slide adjustable. For example, the tibial cuff can be permanently affixed to the stay member and the femoral cuff would slide along the stay for length adjustments and patient comfort. If a pivot 39 as in FIG. 9 is used between the adjuster and the cuff, there is some rocking action and "play" for the cuff relative to the stay member. Accordingly, a cuff may then be affixed to the stay member without any slide adjustment for rocking action only, or the pivot may add a rocking action in addition to the linear adjustment of the cuff.

Figure 7:
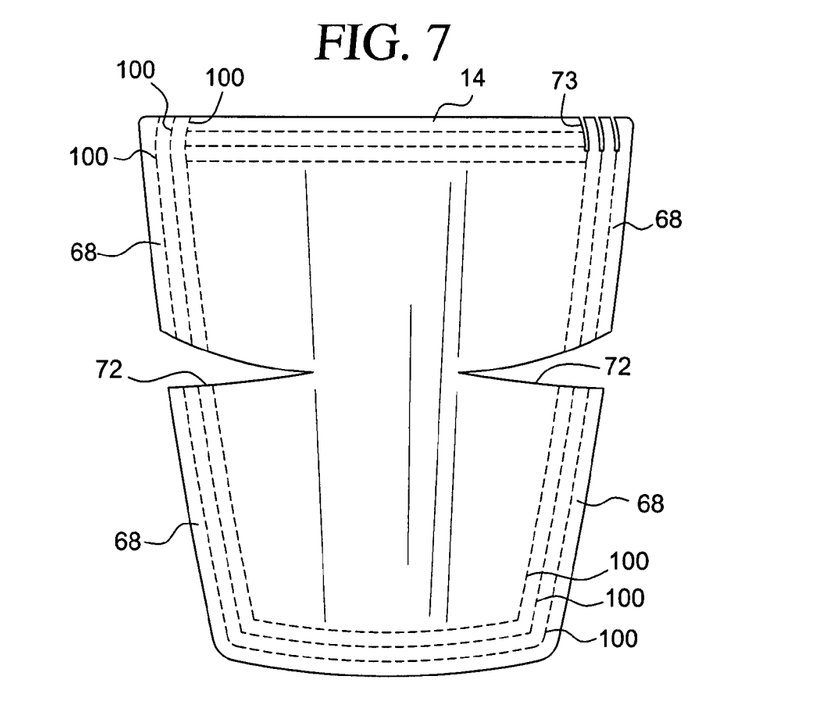
FIG. 7 is a front elevational view of a liner with the panels open.
Figure 8:
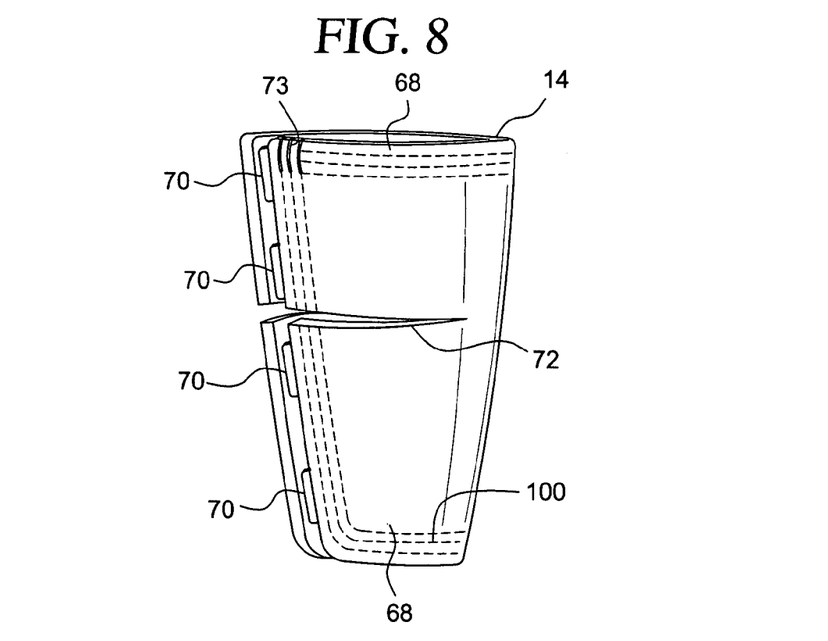
FIG. 8 is a front elevational view of the line of FIG. 7 with the panels closed and secured by hook and loop fasteners.

FIG. 7 shows a preferred embodiment foam compressive liner (i.e., softgood) 14 with four panels 68. The foam liner 14 is made of a non-rigid porous material with UBL (unbroken loop) material laminated to both sides. The UBL can be the same color or different colors to offer color options for the end user. Along one edge of the foam liner 14 are located removably attached hook fastener (e.g., Velcro hooks) tabs 70, as best seen in FIG. 8, which shows the panels 68 folded over and attached to the tabs 70. These tabs 70 can be easily removed, relocated, and reapplied after optional trimming of the foam liner 14 for sizing. During application of the knee immobilizer 10 to the user's leg, the tabs 70 hold the foam liner 14 closed to free up the hands of the end user for securing the straps 16, 18, 20, 22.

Still in FIG. 7, the diameter of the liner 14 at the top is greater than at the bottom to accommodate the greater diameter of the limb above the knee than below the knee. A slit or cut line 72 is provided to relieve the pressure over the patella. Additional slits 73 may be provided as guides for further cutting of this slit when the liner is cut down in width for thinner and/or smaller legs. The patella may protrude through the slit if it is left open, or the patella may be covered by liner material.

In various alternative embodiments, the liner may include size indicia or markings 100 to assist medical practitioners or the user in altering the liner to fit more properly or comfortably. These markings 100 may be perforations cut into the pattern during the die cut stage, or may be printed thereon to give visual guides to the medical practitioners during the trimming and sizing of the softgood liner. An ethylene foam liner may be added to the cuff for added padding and comfort. A patellar cut 72, seen in FIGS. 7 and 8, may be left open or covered in an elastic material that is sewn into the liner. Also, the popliteal pad 32 may be formed into the layers of or sewn into the liner 14 to minimize shifting of the pad 32 in use.

The liner 14 is preferably joined to the stay member 12 and/or one or more cuffs 28, 30 via hook fasteners or Velcro patches. The liner 14 can be a single sheet with pre-cut and pre-shaped panels 68 as depicted in FIG. 7 to nestle against the stay member 12 and one or both cuffs 28, 30. Alternatively, each cuff may have its own discrete sheet of liner material. The liner may be bonded or sewn into the cuff, or be molded into the cuff. In short, the resilience, thickness, number of layers, overall shape, size, panel number and shape, and location of the liner or liners relative to the stay member and cuff can all be customized based on user requirements.

As seen in FIGS. 1 and 9, the knee immobilizer 10 is secured to the leg 24 via a strapping system consisting preferably of four straps, namely, two cuff straps 16, 22 and two stay member straps 18, 20. Two of the straps 16, 22 are permanently attached to the cuffs 28, 30, one on each. The remaining two stay straps 18, 20 are adjustably attached to the rigid stay member 12. That is, each stay strap 18, 20 has an optional loop 74 through which the stay member 12 passes so that the straps can slide and adjust up and down the stay member 12. Naturally, the stay straps 18, 20 can be temporarily or permanently affixed to the stay member 12 if desired by use of hook and loop fasteners, making a knot in the strap, adhesive bonding or welding, or a screw fastener or the like mechanical attachment.

The cuff straps 16, 22 are preferably fastened using a hook and loop arrangement and D-rings 76. It is possible to omit the hook and loop fasteners and simply tie a knot at the D-ring, or more preferably, replace the D-ring with a buckle or a clamp. The buckles may employ a side, top, and/or twist release. The liner 14 is removably attached to the support structure (namely, the stay member 12 and cuffs 28, 30) via strips of Velcro located on the cuffs 28, 30 and the stay straps 18, 20, and can have a hook barrier (not shown) in place during shipping to prevent contact of these hook strips until the knee immobilizer is properly applied to the patient and adjusted. Once the knee immobilizer is fully adjusted and applied, this additional Velcro hook barrier is removed from between the back stay member 12 and the foam liner 14 to allow the Velcro hook on the cuffs 28, 30 and stay straps to grab onto the foam liner and further secure the knee immobilizer.

Figure 10:
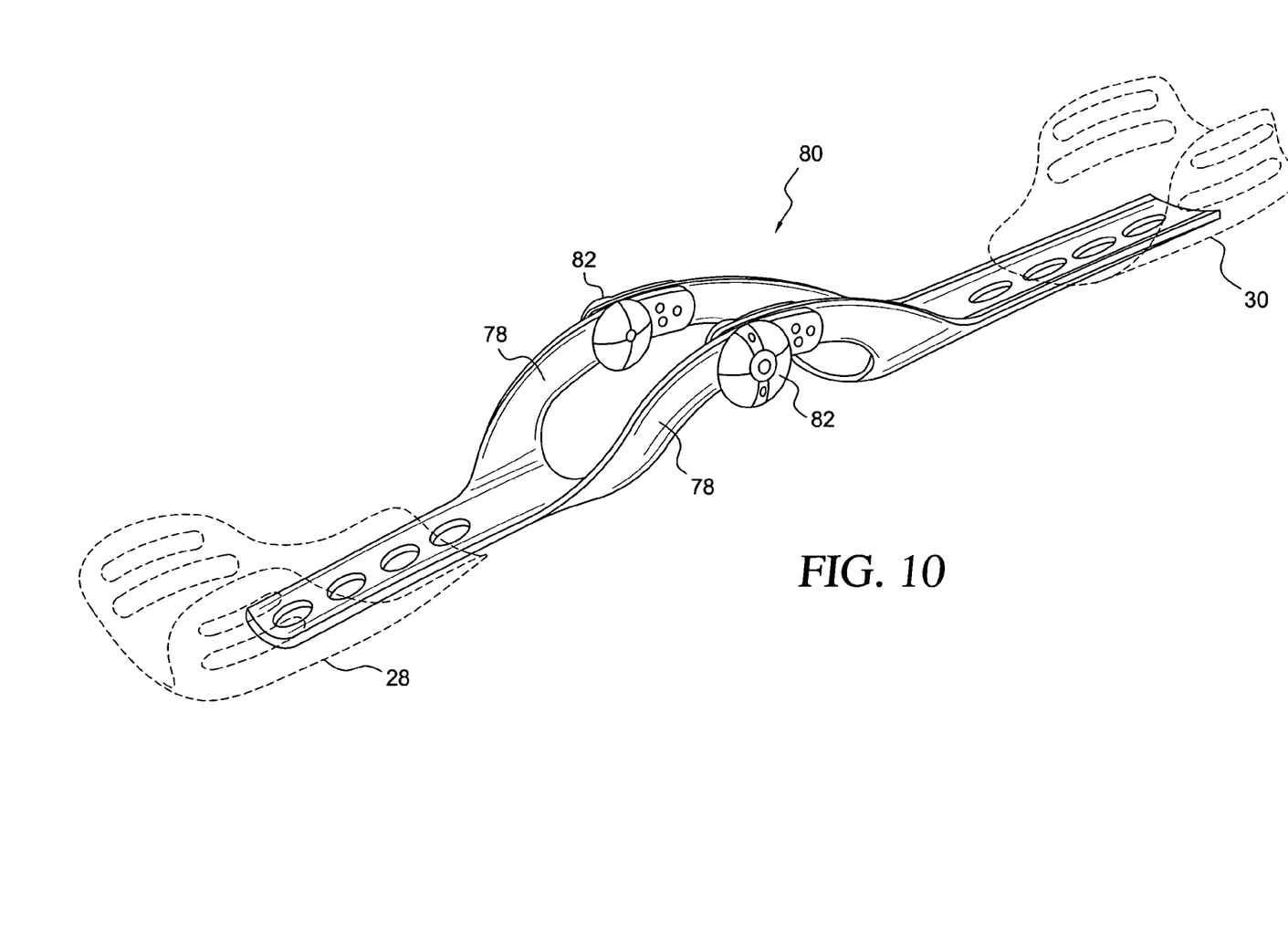
FIG. 10 is a perspective view of an alternative embodiment knee immobilizer.

FIG. 10 is a perspective view of another alternative embodiment stay member 80. The stay member 80 includes the same adjustment means for tibial and femoral cuffs 28, 30 as described above to accommodate various length legs on a brace having range of motion hinges 82 on both sides of the patient's knee. These side mounted hinges 82 can be of the designs shown in, for example, U.S. Pat. No. 5,554,104 (Grim); U.S. Pat. No. D496,464 (Iglesias, et al.); and co-pending U.S. patent application Ser. No. 10/675,324, filed Sep. 29, 2003, titled "Adjustable Ergonomic Knee Brace," by D. Comier et al.; all of whose contents are hereby incorporated by reference. Each hinge 82 is located atop an arch 78 extending from the stay member 80, wherein each arch 78 stretches toward the patella on either side of the knee to better restrain lateral and medial movement. As with the various disclosed embodiments, the brace may include a liner, or be made and worn without a liner with minimal padding on the cuffs and straps. Such a brace, described below, would tailor fit various length legs and would provide a post operative knee brace that would again resist pistoning due to the added fitment of the cuffs as described above.

Figures 11, 12:
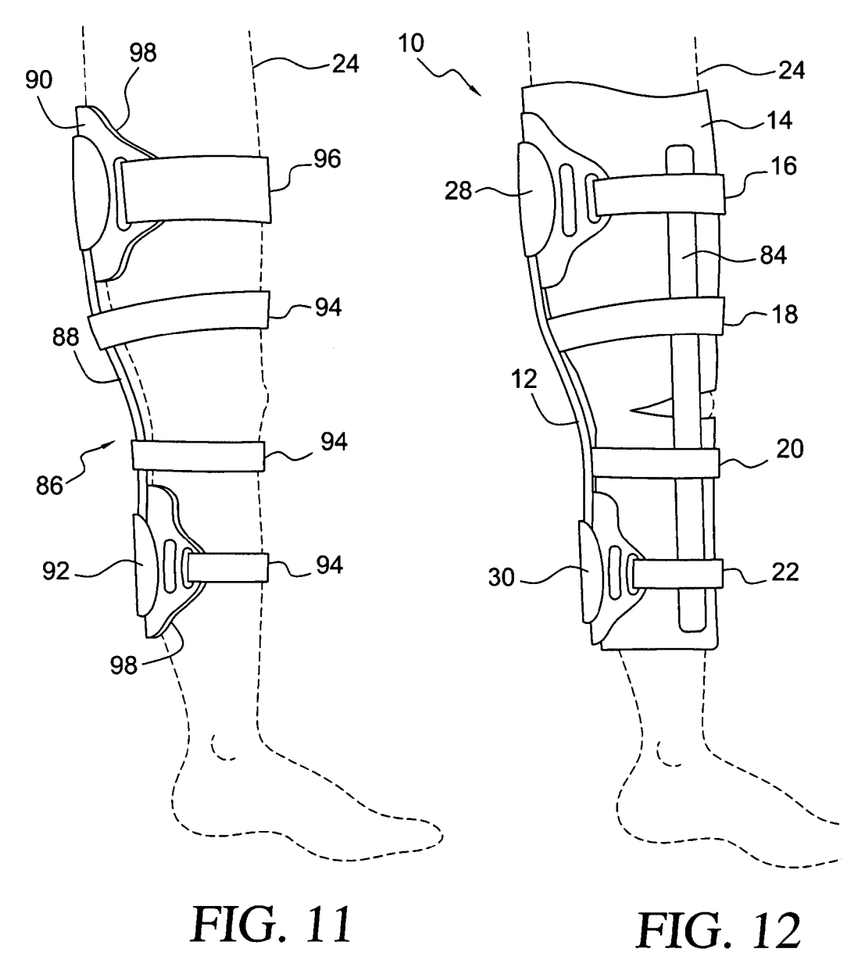
FIG. 11 is a side elevational view of an alternative embodiment knee immobilizer attached to a leg of a patient.
FIG. 12 is a side elevational view of an alternative embodiment knee immobilizer with medial and lateral stay members.

FIG. 11 is a side elevational view of yet another alternative embodiment knee immobilizer 86 for use in warm or humid climates. In this "cool" embodiment, the liner is altogether omitted and/or only a thin layer of liner material 98 is used to pad and cushion the cuffs 90, 92 only. More preferably, the cushioning liner material 98 substantially covers only the areas of the cuffs 90, 92 that touch the patient's leg and does not extend beyond that limited area. The cushioning liner material 98 is further selected to be thinner with less padding as compared to the foam compressive liner 14 shown in FIG. 1, for example.

To be sure, the foam compressive liner 14 in the exemplary embodiment is chosen for its ability to wrap around and stabilize the leg while applying a small amount of compressive pressure to the leg. As such, the compressive liner has a durometer of about 20-35 (using a 302SL sponge rubber gauge). It is known that the knee, ankle, or injured joint when immobilized has a tendency to swell. To minimize this swelling, it is further known in the art that applying the compressive pressure to the leg is beneficial, and hence the use of the compressive liner 14.

On the other hand, the cushioning liner 98 is preferably not made from the softgood liner or UBL material. Rather, the cushioning liner 98 uses a foam or like material of sufficiently high durometer (e.g., durometer of 45-60 using a 302SL sponge rubber gauge) to keep the skin of the wearer from bottoming out in the padding and impacting the cuff. In various preferred embodiments, the cuff cushioning liner 98 is made from a closed cell polyethylene foam, or spacer fabrics and the like. It may have a thickness of about ⅛ to ¼ inch and anything therebetween when mounted to the cuff, while the compressive liner is typically thicker. Further, the closed cell cushioning liner 98 may have a laminate and/or coating thereon to prevent direct contact between foam and skin to reduce sweating.

The "cool" knee immobilizer 86 again includes components such as a rigid stay member 88, one or more length adjustment cuffs 90, 92, and securing straps 94, 96. In this instance, the straps 94, 96 would either be manufactured with a material that does not irritate the skin, or would have some form of padding, coating, or a cushioning liner applied to the skin-facing side. It is optional that the femoral strap 96 have a greater width for a more secure connection to the leg since the compressive liner is omitted. Further, the femoral strap 96 may apply slight compressive pressure on the leg in place of the omitted compressive liner. The wider femoral strap 96 may have a width of about 3-4 inches wide instead of about 2 inches for the other straps 94. Clearly though, any or all of the other straps 94, 96 may have greater widths for the same purposes.

Because the compressive liner has been omitted in this FIG. 11 embodiment, the leg 24 of the patient is mostly open to the ambient air and benefits from the air cooling effect accordingly. Further, without the compressive liner, the knee immobilizer 86 is less bulky, has a lower profile or silhouette, and can more easily fit underneath a patient's pants, rather than over his or her clothing as with most of the conventional products on the market must be worn. Lastly, because the knee immobilizer 86 without a compressive liner allows for a closer, more conforming fit of the cuffs 90, 92 to the muscle belly of patient's leg, the issue of the cuffs unintended pistoning on the leg is virtually eliminated.

FIG. 12 is a side elevational view of the knee immobilizer 10 from FIG. 9 modified with medial and lateral stay members 84. These optional medial and lateral stay members 84 are held in place by straps 16, 18, 20, 22 and overlies the liner 14. More preferably, the medial and lateral stay members 84 are Velcroed, strapped, or otherwise mechanically attached to the liner 14. The primary stay member 12 at the posterior of the leg 24 is still used as are the sliding cuffs 28, 30. When in use, the medial and lateral stay members 84 are located on either side of the injured knee for added medial and lateral support and protection of the knee. For these purposes, the medial and lateral stay members 84 may be made from aluminum bars, rigid plastic strips, or the like, and have a straight length or include a slight bend to follow the contours of the leg.

Although the foregoing exemplary embodiments are described for use on a knee, it is understood that the present invention can be applied to other anatomical joints. From the foregoing detailed description, it should therefore be evident that there are a number of changes, adaptations, and modifications of the present invention that come within the province of those skilled in the art. However, it is intended that all such variations not departing from the spirit of the invention be considered as within the scope thereof except as limited solely by the following claims.

We claim:

1. A knee immobilizer having an adjustable length for supporting the leg of a patient, comprising:
    a continuous and non-interrupted elongated stay member disposed posterior to the leg and having a lengthwise profile that closely approximates a posterior contour of the leg, the stay member having a femoral portion, a tibial portion, and a permanent non-articulating and linear popliteal region therebetween, wherein the stay defines a first curvature whereat the femoral portion merges with the popliteal region, and a second curvature whereat the popliteal region merges with the tibial portion;
    a femoral cuff individually slidably disposed on the femoral portion;
    a tibial cuff individually slidably disposed on the tibial portion;
    at least one liner that at least partially envelopes the leg, disposed on at least one of the stay member, the femoral cuff, and the tibial cuff;
    wherein the femoral and tibial cuffs are selectively adjustable relative to the stay member, the stay member defining a plurality of openings and a button being biased against at least one of the femoral and tibial cuffs and into one of the openings to permit the selective adjustment of the femoral and tibial cuffs along the stay member;
    wherein the first and second curvatures are spaced by the popliteal region, the popliteal region oriented diagonally between parallel and spaced apart first and second reference lines approximating locations of the femoral and tibial portions, respectively, whereat the first and second curvatures lie, respectively, the femoral portion merges at the first curvature orienting the popliteal region toward the second curvature which in turn merges into the tibial portion.

2. The knee immobilizer of claim 1, wherein the means for selectively setting the linear position includes a button biased against at least one cuff into one of a plurality of openings in the stay member.

3. The knee immobilizer of claim 1, wherein at least one of the cuffs and stay member includes markings thereon to indicate sizing information.

4. The knee immobilizer of claim 1, wherein at least one of the cuffs circumscribes at least about 180 degrees of the circumference of the leg to limit rotation of the leg.

5. The knee immobilizer of claim 1, wherein at least one of the cuffs includes a semi-rigid polymer having arms with a window therethrough.

6. The knee immobilizer of claim 1, wherein the liner is a compressive liner having perforations at least partially along a periphery thereof for size trimming.

7. The knee immobilizer of claim 1, wherein at least one of the cuffs includes openings, and a strap passes through the openings and surrounds the leg.

8. The knee immobilizer of claim 1, wherein the liner includes sizing indicia at least partially around its periphery.

9. The knee immobilizer of claim 1, wherein the stay member includes at lest one strap extending circumferentially around the leg and is slidable along the length of the stay member.

10. The knee immobilizer of claim 1, wherein the stay member includes at least one of a medially and a laterally extending struts.

11. The knee immobilizer of claim 1, wherein the stay member includes an articulation located at a posterior portion of the leg and not at the popliteus of the knee.

12. A knee immobilizer having an adjustable length for supporting the leg of a patient, comprising:
- an elongated, rigid stay member having a femoral portion, a tibial portion, and a permanent non-articulating and linear popliteal region generally extending diagonally relative to and between the femoral and tibial portions, the stay member having a lengthwise profile that closely approximates a posterior contour of the leg;
- a popliteal pad attached to the stay member at the popliteal region, the pad having first and second surfaces wherein the first surface is attached to the stay member and the second surface is arranged for being located adjacent to the popliteal region of the knee, a length of popliteal pad delimited by the stay member popliteal region, a width of the popliteal pad extending beyond a periphery of a width of the stay member;
- at least one cuff individually slidably disposed on at least one of the femoral portion and the tibial portion to traverse linearly thereon and arranged to be selectively set at a linear position along the stay member; and
- a cushioning liner that substantially overlies the cuff such that the popliteal pad is interposed between the stay member and the cushioning liner;
- wherein the popliteal region is angled relative to the femoral and tibial portions of the stay member at a functional angle of immobilization of the knee.

13. The knee immobilizer of claim 12, further comprising a wide femoral strap of at least about 3 inches in width disposed on at least one of the stay member and the cuff.

14. The knee immobilizer of claim 12, further comprising a second cuff affixed to the stay member that is immobilized to prevent linear movement along the stay member.

15. The knee immobilizer of claim 12, further comprising at least one wide strap with a cushioning liner on a side facing the leg.

16. The knee immobilizer of claim 12, wherein the cushioning liner includes a polyethylene foam having a durometer of about 45-60 using 302SL sponge rubber gauge.

17. The knee immobilizer of claim 12, wherein the cushioning liner does not extend substantially past an outer periphery of the cuff.

18. A knee immobilizer having an adjustable length for supporting the knee and leg of a patient, comprising:
- an elongated stay member disposed posterior to the leg and having a lengthwise profile that closely approximates a posterior contour of the leg, the stay member having a femoral portion, a tibial portion, and a permanent non-articulating linear popliteal region extending diagonally relative to and between the femoral and tibial portions;
- a curved cuff slidably disposed on at least one of the femoral portion and the tibial portion; and
- at least one liner that at least partially envelopes the leg, disposed on at least one of the stay member and the cuff;
- wherein the femoral and tibial cuffs are selectively adjustable relative to the stay member, the stay member defining a plurality of openings and a button being biased against at least one of the femoral and tibial cuffs and into one of the openings to permit the selective adjustment of the femoral and tibial cuffs along the stay member;
- wherein a cross-section of the stay member defines a bowed shape extending between first and second edges, the stay member having first and second surfaces such that the first surface is arranged to lie against the leg of the patient and the second surface defines a longitudinal recess extending a depth short of the thickness of the stay member.

19. The knee immobilizer of claim 18, further comprising medial and lateral stays disposed on the liner extending along a length of the leg on either side of the knee.

20. The knee immobilizer of claim 18, wherein the liner is joined to at least one of the stay member and the cuff by a removable hook and loop fastener.

21. The knee immobilizer of claim 18, wherein the at least one of the cuff and the liner includes coloring to provide data indicia to the user.

22. The knee immobilizer of claim 18, wherein the cuff includes a pivot to create a pivoting action relative to the stay member.

* * * * *